United States Patent [19]

Lantzsch et al.

[11] Patent Number: 4,719,307

[45] Date of Patent: * Jan. 12, 1988

[54] PROCESS FOR THE PREPARATION OF β-HYDROXYETHYL-(1,2,4-TRIAZOLE) DERIVATIVES

[75] Inventors: Reinhard Lantzsch, Leverkusen; Karl-Julius Reubke, Cologne, both of Fed. Rep. of Germany

[73] Assignee: Bayer Aktiengesellschaft, Leverkusen, Fed. Rep. of Germany

[*] Notice: The portion of the term of this patent subsequent to Jan. 27, 2004 has been disclaimed.

[21] Appl. No.: 916,077

[22] Filed: Oct. 6, 1986

Related U.S. Application Data

[62] Division of Ser. No. 672,553, Nov. 19, 1984, Pat. No. 4,639,527.

[30] Foreign Application Priority Data

Nov. 25, 1983 [DE] Fed. Rep. of Germany ....... 3342693

[51] Int. Cl.[4] ............................................. C07D 249/08
[52] U.S. Cl. ................................................... 548/262
[58] Field of Search ......................................... 548/262

[56] References Cited

U.S. PATENT DOCUMENTS 4,414,210 11/1983 Miller et al. ............... 548/262
4,639,527 1/1987 Lantzsch et al. ........... 548/262

FOREIGN PATENT DOCUMENTS 2920374 11/1980 Fed. Rep. of Germany .

OTHER PUBLICATIONS

J. Heterocyclic Chem., vol. 17, No. 6, 1980 "A New Mesoionic Species in the Synthesis of some 5-Thioxo-1,2,4 . . . Ones".
Journal of The Chemical Society Perkin Transactions I Organic and Bio-Organic Chemistry, No. 5, 1984, pp. 993-998.

*Primary Examiner*—Richard L. Raymond
*Attorney, Agent, or Firm*—Sprung Horn Kramer & Woods

[57] ABSTRACT

The known β-hydroxyethyl-(1,2,4-triazole) derivatives of the formula

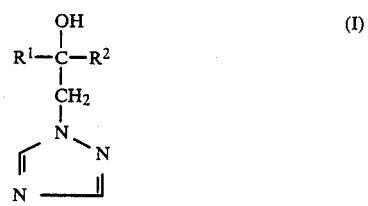

in which
R[1] represents alkyl, halogenoalkyl, alkenyl, alkinyl, optionally substituted cycloalkyl, optionally substituted cycloalkenyl, optionally substituted aryl, optionally substituted aralkyl, optionally substituted aralkenyl or an optionally substituted heterocyclic radical and
R[2] represents hydrogen, alkyl, halogenoalkyl, alkenyl, alkinyl, optionally substituted cycloalkyl, optionally substituted cycloalkenyl, optionally substituted aryl, optionally substituted aralkyl, optionally substituted aralkenyl or an optionally substituted heterocyclic radical, are prepared by a new process, which comprises stirring a β-hydroxyethyl-(1,3,4-triazole) derivative of the formula

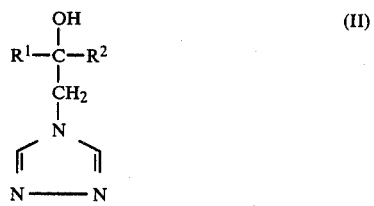

in which
R[1] and R[2] have the abovementional meanings, in the presence of a base and in the presence of an aprotic, dipolar diluent.

9 Claims, No Drawings

PROCESS FOR THE PREPARATION OF β-HYDROXYETHYL-(1,2,4-TRIAZOLE) DERIVATIVES

This is a division, of application Ser. No. 672,553, filed Nov. 19, 1984, now U.S. Pat. No. 4,639,527.

The present invention relates to a new process for the preparation of known β-hydroxyethyl-(1,2,4-triazole) derivatives, which have plant growth-regulating and fungicidal properties.

It has already been disclosed that β-hydroxyethyl-(1,2,4-triazole) derivatives can be prepared by reacting oxiranes with 1,2,4-triazole in the presence of a base and in the presence of inert solvents (compare EP-OS (European Published Specification) No. 40,345, EP-OS (European Published Specification) No. 44,605, EP-OS (European Published Specificatin) No. 46,337, EP-OS (European Published Specification) No. 47,594, EP-OS (European Published Specification) No. 52,424 and DE-OS (German Published Specification) 2,654,890). However, the disadvantage of this process is that, in addition to the 1,2,4-triazole derivatives, greater or lesser amounts of 1,3,4-triazole derivatives are formed, depending on the solvent used. For example, if the reaction is carried out in the presence of alcohols, up to 30% of the undesired substances is formed. These troublesome by-products are expensive to remove and the yields of the desired 1,2,4-triazole derivatives are thus only relatively low.

The present invention now provides a new process for the preparation of a known β-hydroxyethyl-(1,2,4-triazole) derivative of the formula

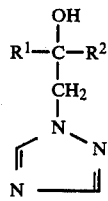
(I)

in which
R¹ represents alkyl, halogenoalkyl, alkenyl, alkinyl, optionally substituted cycloalkyl, optionally substituted cycloalkenyl, optionally substituted aryl, optionally substituted aralkyl, optionally substituted aralkenyl or an optionally substituted heterocyclic radical and
R² represents hydrogen, alkyl, halogenoalkyl, alkenyl, alkinyl, optionally substituted cycloalkyl, optionally substituted cycloalkenyl, optionally substituted aryl, optionally substituted aralkyl, optionally substituted aralkenyl or an optionally substituted heterocyclic radical, which process comprises stirring a β-hydroxyethyl-(1,3,4-triazole) derivative of the formula

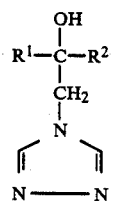
(II)

in which
R¹ and R² have the abovementioned meanings, in the presence of a base and in the presence of an aprotic, dipolar diluent, and, if appropriate, in the presence of a co-catalyst and, if appropriate, in the presence of water, at temperatures between 50° C. and 200° C.

It is to be described as exceptionally surprising that the compounds of the formula (II) can be converted into β-hydroxyethyl-(1,2,4-triazole) derivatives of the formula (I) by the process according to the invention, since such a rearrangement was not yet known from the prior art.

The process according to the invention is distinguished by a number of advantages. Thus, it enables β-hydroxyethyl-(1,2,4-triazole) derivatives of the formula (I) to be prepared in extremely high yields, substances which have hitherto been obtained only as troublesome by-products and which had to be removed being used as starting substances. Furthermore, the reaction is easy to carry out and isolation of the compounds of the formula (I) presents no difficulties at all. It is particularly advantageous here that recrystallisation of the products obtained is not necessary.

If 1-(4-chlorophenyl)-4,4-dimethyl-3-(1,3,4-triazol-1-yl-methyl)-pentan-3-ol is used as the starting substance, sodium hydroxide is used as the base and N-methylpyrrolidone is used as the diluent, the course of the process according to the invention can be illustrated by the following equation:

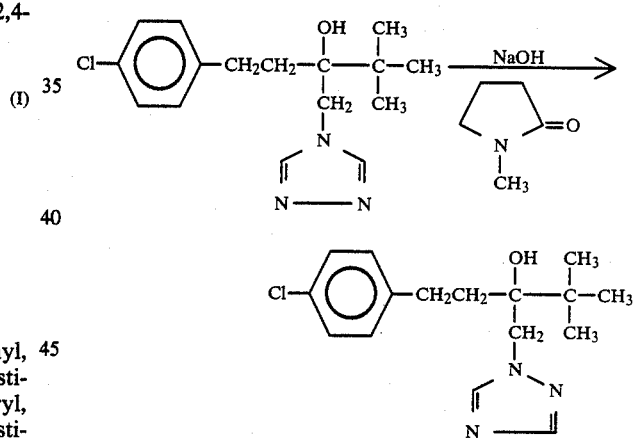

Formula (II) provides a general definition of the β-hydroxyethyl-(1,3,4-triazole) derivatives to be used as starting substances in the process according to the invention. In this formula, R¹ preferably represents straight-chain or branched alkyl with 1 to 8 carbon atoms, straight-chain or branched halogenoalkyl with 1 to 4 carbon atoms and 1 to 5 halogen atoms, alkenyl with 2 to 8 carbon atoms, alkinyl with 2 to 8 carbon atoms, cycloalkyl which has 3 to 7 carbon atoms and is optionally substituted by alkyl with 1 or 2 carbon atoms, cycloalkenyl which has 5 to 8 carbon atoms and is optionally substituted by alkyl with 1 or 2 carbon atoms, or phenyl which is optionally mono-, di- or tri-substituted by identical or different substituents, preferred possible substituents being: halogen, straight-chain or branched alkyl with 1 to 4 carbon atoms, cycloalkyl with 5 to 7 carbon atoms, alkoxy with 1 to 4 carbon atoms, alkylthio with 1 to 4 carbon atoms, halogenoalkyl with 1 or 2 carbon atoms and 1 to 5 halogen atoms, halogenoalkoxy with 1 or 2 carbon atoms and 1 to 5 halogen atoms, halogenoalkylthio with 1 or 2 carbon atoms and 1 to 5 halogen atoms, phenyl which is optionally substituted by halogen and/or alkyl with 1 to 4 carbon atoms, phenoxy which is optionally substituted by halogen and/or alkyl with 1 to 4 carbon atoms, phenylalkyl which has 1 or 2 carbon atoms in the alkyl part and is optionally substituted by halogen and/or alkyl with 1 to 4 carbon atoms, and phenylalkoxy which has 1 or 2 carbon atoms in the alkoxy part and is optionally substituted by halogen and/or alkyl with 1 to 4 carbon atoms. $R^1$ furthermore preferably represents phenylalkyl with 1 to 4 carbon atoms in the alkyl part, it being possible for the phenylalkyl radical to be mono-, di- or tri-substituted in the phenyl part by identical or different substituents from the group comprising halogen, straight-chain or branched alkyl with 1 to 4 carbon atoms, cycloalkyl with 5 to 7 carbon atoms, alkoxy with 1 to 4 carbon atoms, alkylthio with 1 to 4 carbon atoms, halogenoalkyl with 1 or 2 carbon atoms and 1 to 5 halogen atoms, halogenoalkoxy with 1 or 2 carbon atoms and 1 to 5 halogen atoms, halogenoalkylthio with 1 or 2 carbon atoms and 1 to 5 halogen atoms, phenyl which is optionally substituted by halogen and/or alkyl with 1 to 4 carbon atoms, phenoxy which is optionally substituted by halogen and/or alkyl with 1 to 4 carbon atoms, phenylalkyl which has 1 or 2 carbon atoms in the alkyl part and is optionally substituted by halogen and/or alkyl with 1 to 4 carbon atoms and/or phenylalkoxy which has 1 or 2 carbon atoms in the alkoxy part and is optionally substituted by halogen and/or alkyl with 1 to 4 carbon atoms. $R^1$ furthermore preferably represents phenylalkenyl with 2 to 4 carbon atoms in the alkenyl part, it being possible for the phenylalkenyl radical to be mono-, di- or tri-substituted in the phenyl part by identical or different substituents from the group comprising halogen, straight-chain or branched alkyl with 1 to 4 carbon atoms, cycloalkyl with 5 to 7 carbon atoms, alkoxy with 1 to 4 carbon atoms, alkylthio with 1 to 4 carbon atoms, halogenoalkyl with 1 or 2 carbon atoms and 1 to 5 halogen atoms, halogenoalkoxy with 1 or 2 carbon atoms and 1 to 5 halogen atoms, halogenoalkylthio with 1 or 2 carbon atoms and 1 to 5 halogen atoms, phenyl which is optionally substituted by halogen and/or alkyl with 1 to 4 carbon atoms, phenoxy which is optionally substituted by halogen and/or alkyl with 1 to 4 carbon atoms, phenylalkyl which has 1 or 2 carbon atoms in the alkyl part and is optionally substituted by halogen and/or alkyl with 1 to 4 carbon atoms, and/or phenylalkoxy which has 1 or 2 carbon atoms in the alkyl part and is optionally substituted by halogen and/or alkyl with 1 to 4 carbon atoms. $R^1$ moreover preferably represents a heterocyclic radical which has 5 to 7 ring members and 1 to 3 hetero-atoms, such as oxygen, sulphur and/or nitrogen, and is optionally substituted by halogen and/or alkyl with 1 to 4 carbon atoms. $R^2$ in formula (II) preferably represents hydrogen, straight-chain or branched alkyl with 1 to 8 carbon atoms, straight-chain or branched halogenoalkyl with 1 to 4 carbon atoms and 1 to 5 halogen atoms, alkenyl with 2 to 8 carbon atoms, alkinyl with 2 to 8 carbon atoms, cycloalkyl which has 3 to 7 carbon atoms and is optionally substituted by alkyl with 1 or 2 carbon atoms, cycloalkenyl which has 5 to 8 carbon atoms and is optionally substituted by alkyl with 1 or 2 carbon atoms, or phenyl which is optionally mono-, di- or tri-substituted by identical or different substituents, preferred possible substituents being: halogen, straight-chain or branched alkyl with 1 to 4 carbon atoms, cycloalkyl with 5 to 7 carbon atoms, alkoxy with 1 to 4 carbon atoms, alkylthio with 1 to 4 carbon atoms, halogenoalkyl with 1 or 2 carbon atoms and 1 to 5 halogen atoms, halogenoalkoxy with 1 or 2 carbon atoms and 1 to 5 halogen atoms, halogenoalkylthio with 1 or 2 carbon atoms and 1 to 5 halogen atoms, phenyl which is optionally substituted by halogen and/or alkyl with 1 to 4 carbon atoms, phenoxy which is optionally substituted by halogen and/or alkyl with 1 to 4 carbon atoms, phenylalkyl which has 1 or 2 carbon atoms in the alkyl part and is optionally substituted by halogen and/or alkyl with 1 to 4 carbon atoms, and phenylalkoxy which has 1 or 2 carbon atoms in the alkoxy part and is optionally substituted by halogen and/or alkyl with 1 to 4 carbon atoms. $R^2$ furthermore preferably represents phenylalkyl with 1 to 4 carbon atoms in the alkyl part, it being possible for the phenylalkyl radical to be mono-, di- or tri-substituted in the phenyl part by identical or different substituents from the group comprising halogen, straight-chain or branched alkyl with 1 to 4 carbon atoms, cycloalkyl with 5 to 7 carbon atoms, alkoxy with 1 to 4 carbon atoms, alkylthio with 1 to 4 carbon atoms, halogenoalkyl with 1 or 2 carbon atoms and 1 to 5 halogen atoms, halogenoalkoxy with 1 or 2 carbon atoms and 1 to 5 halogen atoms, halogenoalkylthio with 1 or 2 carbon atoms and 1 to 5 halogen atoms, phenyl which is optionally substituted by halogen and/or alkyl with 1 to 4 carbon atoms, phenoxy which is optionally substituted by halogen and/or alkyl with 1 to 4 carbon atoms, phenylalkyl which has 1 or 2 carbon atoms in the alkyl part and is optionally substituted by halogen and/or alkyl with 1 to 4 carbon atoms and/or phenylalkoxy which has 1 or 2 carbon atoms in the alkoxy part and is optionally substituted by halogen and/or alkyl with 1 to 4 carbon atoms. $R^2$ furthermore preferably represents phenylalkenyl with 2 to 4 carbon atoms in the alkenyl part, it being possible for the phenylalkenyl radical to be mono-, di- or tri-substituted in the phenyl part by identical or different substituents from the group comprising halogen, straight-chain or branched alkyl with 1 to 4 carbon atoms, cycloalkyl with 5 to 7 carbon atoms, alkoxy with 1 to 4 carbon atoms, alkylthio with 1 to 4 carbon atoms, halogenoalkyl with 1 or 2 carbon atoms and 1 to 5 halogen atoms, halogenoalkoxy with 1 or 2 carbon atoms and 1 to 5 halogen atoms, halogenoalkylthio with 1 or 2 carbon atoms and 1 to 5 halogen atoms, phenyl which is optionally substituted by halogen and/or alkyl with 1 to 4 carbon atoms, phenoxy which is optionally substituted by halogen and/or alkyl with 1 to 4 carbon atoms, phenylalkyl which has 1 or 2 carbon atoms in the alkyl part and is optionally substituted by halogen and/or alkyl with 1 to 4 carbon atoms, and/or phenylalkoxy which has 1 or 2 carbon atoms in the alkyl part and is optionally substituted by halogen and/or alkyl with 1 to 4 carbon atoms. $R^2$ moreover preferably represents a heterocyclic radical which has 5 to 7 ring members and 1 to 3 hetero-atoms, such as oxygen, sulphur and/or nitrogen, and is optionally substituted by halogen and/or alkyl with 1 to 4 carbon atoms.

Particularly preferred starting substances are those compounds of the formula (II) in which
$R^1$ represents methyl, ethyl, propyl, isopropyl, n-butyl, iso-butyl, sec.-butyl, or tert.-butyl, or methyl, ethyl, propyl, isopropyl, n-butyl, iso-butyl, sec.-butyl or tert.-butyl which is substituted by 1 to 3 fluorine and/or chlorine atoms, or represents alkenyl with 2 to 6 carbon atoms, alkinyl with 2 to 6 carbon atoms, or cyclopropyl, cyclopentyl or cyclohexyl which is optionally substituted by methyl, or cyclopentenyl, cyclohexenyl, cycloheptenyl or cyclooctenyl which is optionally substituted by methyl, or represents phenyl, which can be mono-, di- or tri-substituted by fluorine, chlorine, bromine, methyl, tert.-butyl, cyclohexyl, methoxy, methylthio, trifluoromethyl, trifluoromethoxy, trifluoromethylthio, phenyl which is optionally substituted by fluorine, chlorine and/or methyl, phenoxy which is optionally substituted by fluorine, chlorine and/or methyl, benzyl which is optionally substituted by fluorine, chlorine and/or methyl and/or benzyloxy which is optionally substituted by fluorine, chlorine and/or methyl, or represents phenethyl, which can be 1-, 2- or 3-substituted in the phenyl part by fluorine, chlorine, bromine, methyl, tert.-butyl, cyclohexyl, methoxy, methylthio, trifluoromethyl, tri-fluoromethoxy, trifluoromethylthio, phenyl which is optionally substituted by fluorine, chlorine and/or methyl, phenoxy which is optionally substituted by fluorine, chlorine and/or methyl, benzyl which is optionally substituted by fluorine, chlorine and/or methyl and/or benzyloxy which is optionally substituted by fluorine, chlorine and/or methyl, or represents 2-phenyl-ethenyl, which can be 1-, 2- or 3-substituted in the phenyl part by fluorine, chlorine, bromine, methyl, tert.-butyl, cyclohexyl, methoxy, methylthio, trifluoromethyl, trifluoromethoxy, trifluoromethylthio, phenyl which is optionally substituted by fluorine, chlorine and/or methyl, phenoxy which is optionally substituted by fluorine, chlorine and/or methyl, benzyl which is optionally substituted by fluorine, chlorine and/or methyl and/or benzyloxy which is optionally substituted by fluorine, chlorine and/or methyl, or represents furanyl, thiophenyl, pyridinyl, pyrimidinyl or pyrrolyl, which is optionally substituted by chlorine and/or methyl, and R² represents hydrogen, methyl, ethyl, propyl, isopropyl, n-butyl, iso-butyl, sec.-butyl or tert.-butyl, or methyl, ethyl, propyl, isopropyl, n-butyl, iso-butyl, sec.-butyl or tert.-butyl which is substituted by 1 to 3 fluorine and/or chlorine atoms, or represents alkenyl with 2 to 6 carbon atoms, alkinyl with 2 to 6 carbon atoms, or cyclopropyl, cyclopentyl or cyclohexyl which is optionally substituted by methyl, or cyclopentenyl, cyclohexenyl, cycloheptenyl or cyclooctenyl which is optionally substituted by methyl, or represents phenyl, which can be mono-, di- or tri-substituted by fluorine, chlorine, bromine, methyl, tert.-butyl, cyclohexyl, methoxy, methylthio, trifluoromethyl, trifluoromethoxy, trifluoromethylthio, phenyl which is optionally substituted by fluorine, chlorine and/or methyl, phenoxy which is optionally substituted by fluorine, chlorine and/or methyl, benzyl which is optionally substituted by fluorine, chlorine and/or methyl and/or benzyloxy which is optionally substituted by fluorine, chlorine and/or methyl, or represents phenethyl, which can be 1-, 2- or 3-substituted in the phenyl part by fluorine, chlorine, bromine, methyl, tert.-butyl, cyclohexyl, methoxy, methylthio, trifluoromethyl, trifluoromethoxy, trifluoromethylthio, phenyl which is optionally substituted by fluorine, chlorine and/or methyl, phenoxy which is optionally substituted by fluorine, chlorine and/or methyl, benzyl which is optionally substituted by fluorine, chlorine and/or methyl and/or benzyloxy which is optionally substituted by fluorine, chlorine and/or methyl, or represents 2-phenyl-ethenyl, which can be 1-, 2- or 3-substituted in the phenyl part by fluorine, chlorine, bromine, methyl, tert.-butyl, cyclohexyl, methoxy, methylthio, trifluoromethyl, trifluoromethoxy, trifluoromethylthio, phenyl which is optionally substituted by fluorine, chlorine and/or methyl, phenoxy which is optionally substituted by fluorine, chlorine and/or methyl, benzyl which is optionally substituted by fluorine, chlorine and/or methyl and/or benzyloxy which is optionally substituted by fluorine, chlorine and/or methyl, or represents furanyl, thiophenyl, pyridinyl, pyrimidinyl, or pyrrolyl, which is optionally substituted by chlorine and/or methyl.

The substances listed by way of their formulae in the table which follows may be mentioned as examples of β-hydroxyethyl-(1,3,4-triazole) derivatives of the formula (II).

TABLE 1

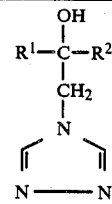

TABLE 1-continued $$\underset{\underset{\underset{N\phantom{=}\phantom{=}N}{\diagdown\phantom{xx}\diagup}}{\underset{N}{|}}}{\overset{\overset{OH}{|}}{\underset{|}{R^1-C-R^2}}}\phantom{xx}(II)$$

| R¹ | R² |
|---|---|
| CH₃—C₆H₄—CH₂—CH₂— | " |
| Cl,Cl—C₆H₃—CH₂—CH₂— | " |
| F₃C—C₆H₄—CH₂—CH₂— | " |
| F₃CO—C₆H₄—CH₂—CH₂— | " |
| F₃CS—C₆H₄—CH₂—CH₂— | " |
| H₃CS—C₆H₄—CH₂—CH₂— | " |
| (CH₃)₃C—C₆H₄—CH₂—CH₂— | " |
| C₆H₅—C₆H₄—CH₂—CH₂— | —C₆H₄—Cl |
| Cl—C₆H₄—C₆H₄—CH₂—CH₂— | " |
| C₆H₅—O—C₆H₄—CH₂—CH₂— | " |
| Cl—C₆H₄—O—C₆H₄—CH₂—CH₂— | " |
| C₆H₅—CH₂—C₆H₄—CH₂—CH₂— | " |
| Cl—C₆H₄—CH₂—C₆H₄—CH₂—CH₂— | " |
| C₆H₅—CH₂—O—C₆H₄—CH₂—CH₂— | " |
| Cl—C₆H₄—CH₂—O—C₆H₄—CH₂—CH₂— | " |
| Cl—C₆H₄—CH₂—CH₂— | " |
| F—C₆H₄—CH₂—CH₂— | " |

TABLE 1-continued $$\underset{\underset{\underset{N\phantom{=}\phantom{=}N}{\diagdown\phantom{xx}\diagup}}{\underset{N}{|}}}{\overset{\overset{OH}{|}}{\underset{|}{R^1-C-R^2}}}\phantom{xx}(II)$$

| R¹ | R² |
|---|---|
| CH₃—C₆H₄—CH₂—CH₂— | " |
| Cl,Cl—C₆H₃—CH₂—CH₂— | " |
| F₃C—C₆H₄—CH₂—CH₂— | " |
| F₃CO—C₆H₄—CH₂—CH₂— | " |
| F₃CS—C₆H₄—CH₂—CH₂— | " |
| H₃CS—C₆H₄—CH₂—CH₂— | " |
| (CH₃)₃C—C₆H₄—CH₂—CH₂— | " |
| C₆H₅—C₆H₄—CH₂—CH₂— | —CH(CH₃)₂ |
| Cl—C₆H₄—C₆H₄—CH₂—CH₂— | " |
| C₆H₅—O—C₆H₄—CH₂—CH₂— | " |
| Cl—C₆H₄—O—C₆H₄—CH₂—CH₂— | " |
| C₆H₅—CH₂—C₆H₄—CH₂—CH₂— | " |
| Cl—C₆H₄—CH₂—C₆H₄—CH₂—CH₂— | " |
| C₆H₅—CH₂—O—C₆H₄—CH₂—CH₂— | " |
| Cl—C₆H₄—CH₂—O—C₆H₄—CH₂—CH₂— | " |
| Cl—C₆H₄—CH₂—CH₂— | " |
| F—C₆H₄—CH₂—CH₂— | " |

TABLE 1-continued $$\begin{array}{c} \text{OH} \\ R^1-\overset{|}{\underset{|}{C}}-R^2 \\ CH_2 \\ | \\ N \\ \diagup \diagdown \\ N=\!\!=\!\!N \end{array} \quad (II)$$

| R¹ | R² |
|---|---|
| CH₃—⟨C₆H₄⟩—CH₂—CH₂— | " |
| 3,4-Cl₂—⟨C₆H₃⟩—CH₂—CH₂— | " |
| F₃C—⟨C₆H₄⟩—CH₂—CH₂— | " |
| F₃CO—⟨C₆H₄⟩—CH₂—CH₂— | " |
| F₃CS—⟨C₆H₄⟩—CH₂—CH₂— | " |
| H₃CS—⟨C₆H₄⟩—CH₂—CH₂— | " |
| (CH₃)₃C—⟨C₆H₄⟩—CH₂—CH₂— | " |
| ⟨C₆H₅⟩—⟨C₆H₄⟩—CH₂—CH₂— | cyclohexyl |
| Cl—⟨C₆H₄⟩—⟨C₆H₄⟩—CH₂—CH₂— | " |
| ⟨C₆H₅⟩—O—⟨C₆H₄⟩—CH₂—CH₂— | cyclohexyl |
| Cl—⟨C₆H₄⟩—O—⟨C₆H₄⟩—CH₂—CH₂— | " |
| ⟨C₆H₅⟩—CH₂—⟨C₆H₄⟩—CH₂—CH₂— | " |
| Cl—⟨C₆H₄⟩—CH₂—⟨C₆H₄⟩—CH₂—CH₂— | " |
| ⟨C₆H₅⟩—CH₂—O—⟨C₆H₄⟩—CH₂—CH₂— | " |
| Cl—⟨C₆H₄⟩—CH₂—O—⟨C₆H₄⟩—CH₂—CH₂— | " |
| Cl—⟨C₆H₄⟩—CH₂—CH₂— | " |
| F—⟨C₆H₄⟩—CH₂—CH₂— | " |
| CH₃—⟨C₆H₄⟩—CH₂—CH₂— | " |
| 3,4-Cl₂—⟨C₆H₃⟩—CH₂—CH₂— | " |
| F₃C—⟨C₆H₄⟩—CH₂—CH₂— | " |
| F₃CO—⟨C₆H₄⟩—CH₂—CH₂— | " |
| F₃CS—⟨C₆H₄⟩—CH₂—CH₂— | " |
| H₃CS—⟨C₆H₄⟩—CH₂—CH₂— | " |
| (CH₃)₃C—⟨C₆H₄⟩—CH₂—CH₂— | " |
| ⟨C₆H₅⟩—⟨C₆H₄⟩—CH₂—CH₂— | 1-methylcyclopropyl |
| Cl—⟨C₆H₄⟩—⟨C₆H₄⟩—CH₂—CH₂— | " |
| ⟨C₆H₅⟩—O—⟨C₆H₄⟩—CH₂—CH₂— | " |
| Cl—⟨C₆H₄⟩—O—⟨C₆H₄⟩—CH₂—CH₂— | " |
| ⟨C₆H₅⟩—CH₂—⟨C₆H₄⟩—CH₂—CH₂— | " |
| Cl—⟨C₆H₄⟩—CH₂—⟨C₆H₄⟩—CH₂—CH₂— | " |
| ⟨C₆H₅⟩—CH₂—O—⟨C₆H₄⟩—CH₂—CH₂— | " |
| Cl—⟨C₆H₄⟩—CH₂—O—⟨C₆H₄⟩—CH₂—CH₂— | " |
| Cl—⟨C₆H₄⟩—CH₂—CH₂— | " |
| F—⟨C₆H₄⟩—CH₂—CH₂— | " |

TABLE 1-continued $$\underset{\underset{\underset{N\text{———}N}{\overset{|}{\underset{N}{\big|}}}}{\overset{CH_2}{\big|}}}{\overset{OH}{\underset{|}{R^1-C-R^2}}} \quad (II)$$

| R¹ | R² |
|---|---|
| CH₃-C₆H₄-CH₂-CH₂- | " |
| Cl-C₆H₄-CH₂-CH₂- | " |
| F₃C-C₆H₄-CH₂-CH₂- | " |
| F₃CO-C₆H₄-CH₂-CH₂- | " |
| F₃CS-C₆H₄-CH₂-CH₂- | " |
| H₃CS-C₆H₄-CH₂-CH₂- | " |
| (CH₃)₃C-C₆H₄-CH₂-CH₂- | " |
| C₆H₅-C₆H₄-CH=CH- | -C(CH₃)₃ |
| Cl-C₆H₄-C₆H₄-CH=CH- | " |
| C₆H₅-O-C₆H₄-CH=CH- | " |
| Cl-C₆H₄-O-C₆H₄-CH=CH- | " |
| C₆H₅-CH₂-C₆H₄-CH=CH- | " |
| Cl-C₆H₄-CH₂-C₆H₄-CH=CH- | " |
| C₆H₅-CH₂-O-C₆H₄-CH=CH- | " |
| Cl-C₆H₄-CH₂-O-C₆H₄-CH=CH- | " |
| Cl-C₆H₄-CH=CH- | " |
| F-C₆H₄-CH=CH- | " |

TABLE 1-continued $$\underset{\underset{\underset{N\text{———}N}{\overset{|}{\underset{N}{\big|}}}}{\overset{CH_2}{\big|}}}{\overset{OH}{\underset{|}{R^1-C-R^2}}} \quad (II)$$

| R¹ | R² |
|---|---|
| CH₃-C₆H₄-CH=CH- | " |
| Cl,Cl-C₆H₃-CH=CH- | " |
| F₃C-C₆H₄-CH=CH- | " |
| F₃CO-C₆H₄-CH=CH- | " |
| F₃CS-C₆H₄-CH=CH- | " |
| H₃CS-C₆H₄-CH=CH- | " |
| (CH₃)₃C-C₆H₄-CH=CH- | " |
| C₆H₅-C₆H₄-CH=CH- | -C₆H₄-Cl |
| Cl-C₆H₄-C₆H₄-CH=CH- | " |
| C₆H₅-O-C₆H₄-CH=CH- | " |
| Cl-C₆H₄-O-C₆H₄-CH=CH- | " |
| C₆H₅-CH₂-C₆H₄-CH=CH- | " |
| Cl-C₆H₄-CH₂-C₆H₄-CH=CH- | " |
| C₆H₅-CH₂-O-C₆H₄-CH=CH- | " |
| Cl-C₆H₄-CH₂-O-C₆H₄-CH=CH- | " |
| Cl-C₆H₄-CH=CH- | " |
| F-C₆H₄-CH=CH- | " |

TABLE 1-continued $$\underset{\underset{\underset{N \diagdown N}{\diagup}}{\overset{|}{\underset{CH_2}{C}}}}{\overset{OH}{\underset{|}{C}}}R^2 \quad (II)$$

| $R^1$ | $R^2$ |
|---|---|
| CH₃—C₆H₄—CH=CH— | " |
| 3,4-Cl₂—C₆H₃—CH=CH— | " |
| F₃C—C₆H₄—CH=CH— | " |
| F₃CO—C₆H₄—CH=CH— | " |
| F₃CS—C₆H₄—CH=CH— | " |
| H₃CS—C₆H₄—CH=CH— | " |
| (CH₃)₃C—C₆H₄—CH=CH— | " |
| C₆H₅—C₆H₄—CH=CH— | —CH(CH₃)₂ |
| Cl—C₆H₄—C₆H₄—CH=CH— | " |
| C₆H₅—O—C₆H₄—CH=CH— | " |
| Cl—C₆H₄—O—C₆H₄—CH=CH— | " |
| C₆H₅—CH₂—C₆H₄—CH=CH— | " |
| Cl—C₆H₄—CH₂—C₆H₄—CH=CH— | " |
| C₆H₅—CH₂—O—C₆H₄—CH=CH— | " |
| Cl—C₆H₄—CH₂—O—C₆H₄—CH=CH— | " |
| Cl—C₆H₄—CH=CH— | " |
| F—C₆H₄—CH=CH— | " |

TABLE 1-continued $$\underset{\underset{\underset{N \diagdown N}{\diagup}}{\overset{|}{\underset{CH_2}{C}}}}{\overset{OH}{\underset{|}{C}}}R^2 \quad (II)$$

| $R^1$ | $R^2$ |
|---|---|
| CH₃—C₆H₄—CH=CH— | " |
| 3,4-Cl₂—C₆H₃—CH=CH— | " |
| F₃C—C₆H₄—CH=CH— | " |
| F₃CO—C₆H₄—CH=CH— | " |
| F₃CS—C₆H₄—CH=CH— | " |
| H₃CS—C₆H₄—CH=CH— | " |
| (CH₃)₃C—C₆H₄—CH=CH— | " |
| C₆H₅—C₆H₄—CH=CH— | —C₆H₁₁ |
| Cl—C₆H₄—C₆H₄—CH=CH— | " |
| C₆H₅—O—C₆H₄—CH=CH— | " |
| Cl—C₆H₄—O—C₆H₄—CH=CH— | " |
| C₆H₅—CH₂—C₆H₄—CH=CH— | " |
| Cl—C₆H₄—CH₂—C₆H₄—CH=CH— | " |
| C₆H₅—CH₂—O—C₆H₄—CH=CH— | " |
| Cl—C₆H₄—CH₂—O—C₆H₄—CH=CH— | " |
| Cl—C₆H₄—CH=CH— | " |
| F—C₆H₄—CH=CH— | " |

TABLE 1-continued

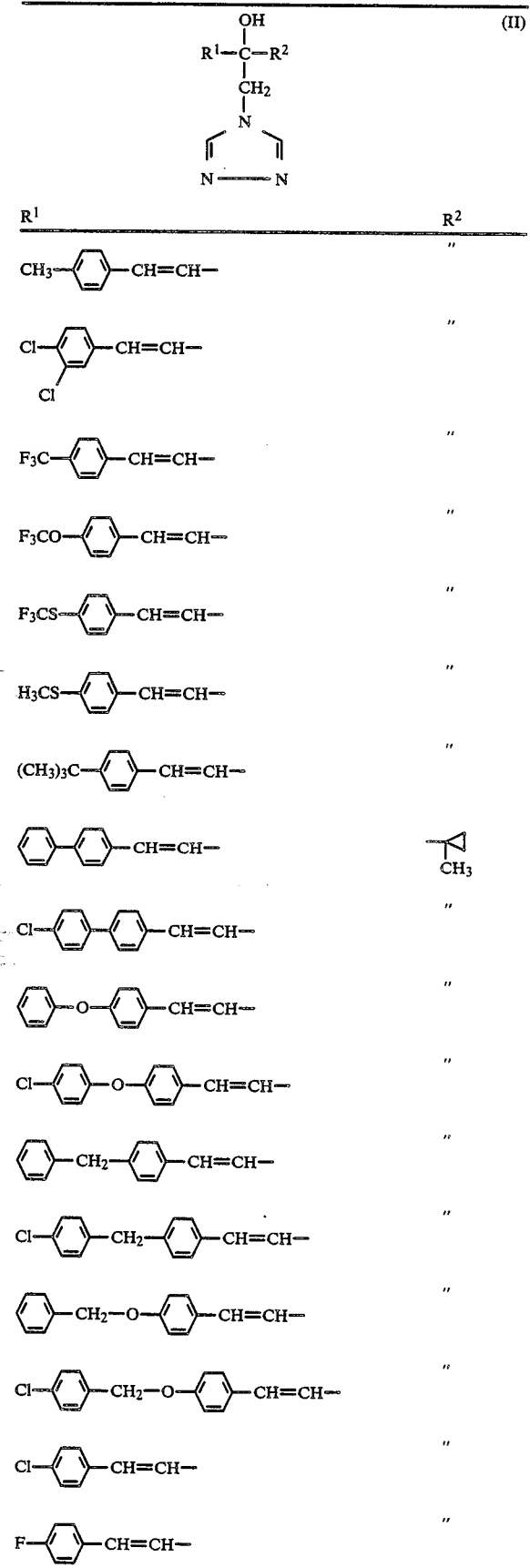

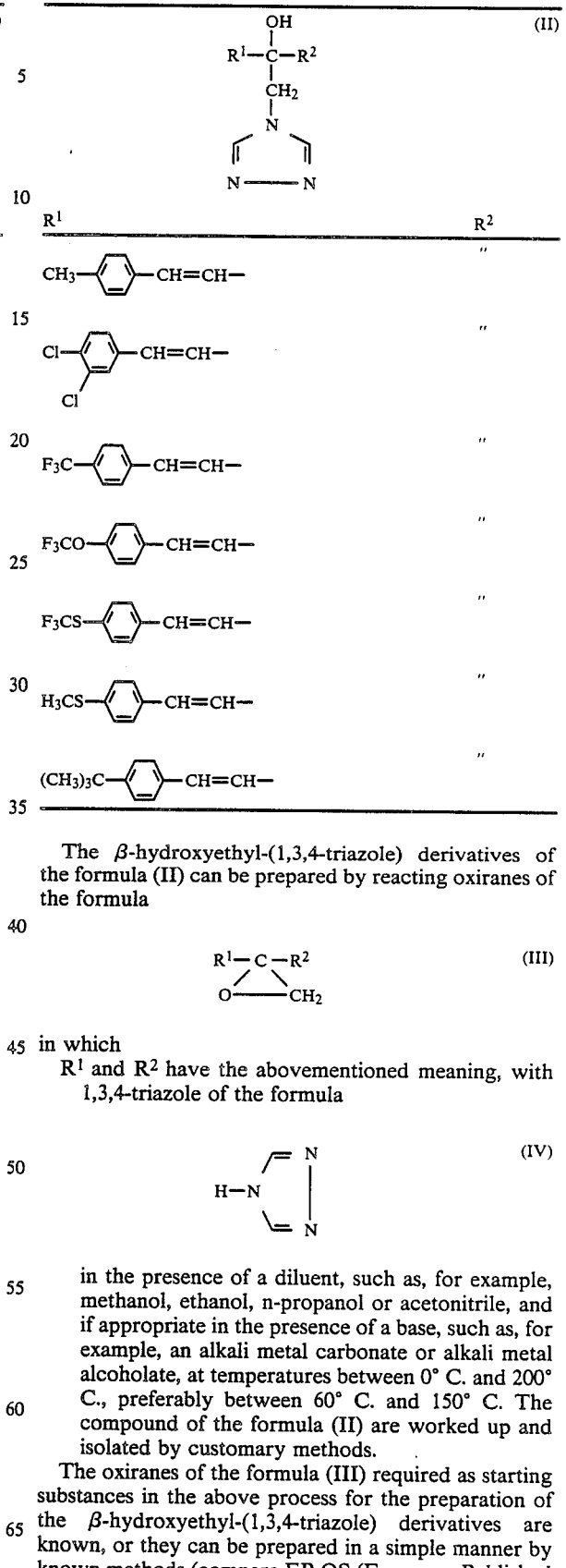

The β-hydroxyethyl-(1,3,4-triazole) derivatives of the formula (II) can be prepared by reacting oxiranes of the formula $$\underset{O\underline{\qquad}CH_2}{R^1-C-R^2} \qquad (III)$$

in which
R$^1$ and R$^2$ have the abovementioned meaning, with 1,3,4-triazole of the formula $$H-N\diagup\hspace{-0.3em}\diagdown\hspace{-0.3em}\begin{array}{c}N\\|\\N\end{array} \qquad (IV)$$

in the presence of a diluent, such as, for example, methanol, ethanol, n-propanol or acetonitrile, and if appropriate in the presence of a base, such as, for example, an alkali metal carbonate or alkali metal alcoholate, at temperatures between 0° C. and 200° C., preferably between 60° C. and 150° C. The compound of the formula (II) are worked up and isolated by customary methods.

The oxiranes of the formula (III) required as starting substances in the above process for the preparation of the β-hydroxyethyl-(1,3,4-triazole) derivatives are known, or they can be prepared in a simple manner by known methods (compare EP-OS (European Published Specification) No. 40,345, EP-OS (European Published Specification) No. 46,337 and EP-OS (European Published Specification) No. 52,424).

Possible bases for the reaction according to the invention are all the inorganic and organic bases which can usually be employed. Bases which can preferably be used are alkali metal carbonates, such as sodium carbonate and potassium carbonate, and furthermore alkali metal hydroxides and alkaline earth metal hydroxides and oxides, such as lithium hydroxide, sodium hydroxide, potassium hydroxide, calcium hydroxide and calcium oxide, and moreover alkali metal alcoholates, such as sodium methylate, sodium ethylate, sodium isobutylate and potassium tert.-butylate, and in addition also lower tertiary alkylamines, cycloalkylamines and aralkylamines, such as, in particular, triethylamine. Bases which can especially preferably be used are sodium hydroxide and potassium hydroxide.

Diluents which can be used in carrying out the process according to the invention are aprotic, dipolar solvents which are stable towards the bases. Preferred solvents are N,N'-dimethylformamide, N,N-dimethylacetamide, dimethyl sulphone, dimethylsulphoxide, hexamethylphosphoric acid triamide, phospholine oxides, such as 1-oxo-1-methyl-phospholine, and furthermore sulpholane, tetramethylurea, N-methylpyrrolidone, N-methyl-hexahydropyridone, 1,3-dimethyl-hexahydro-pyrimidone and N-methyl-ε-caprolactam. N-Methyl-pyrrolidone can especially preferably be used.

The process according to the invention is preferably carried out in the presence of a co-catalyst. Possible co-catalysts here are all the compounds which can form free radicals. Examples which may be mentioned are azobisisobutyronitrile and benzoyl peroxide. It is also possible to pass air or oxygen through the reaction mixture.

In some cases, it is advantageous to carry out the reaction according to the invention in the presence of a small amount of water in order thus to achieve a better solubility of the base employed.

In carrying out the process according to the invention, the reaction temperatures can be varied within a substantial range. In general, the reaction is carried out at temperatures between 50° and 200° C., preferably between 70° and 150° C.

The process according to the invention is in general carried out under normal pressure. However, it is also possible to carry out the reaction under increased or reduced pressure.

In carrying out the process according to the invention, in general 0.01 to 1 mole, preferably 0.1 to 0.5 mole, of base and an adequate amount of aprotic, dipolar diluent are employed per mole of β-hydroxyethyl-(1,3,4-triazole) derivative of the formula (II).

If a co-catalyst is used, this is added in amounts of 0.01 to 1 percent by weight, based on the β-hydroxyethyl-(1,3,4-triazole) derivative of the formula (II) employed. If water is used as an auxiliary solvent, only traces of this are added. In general, water is used in amounts of 0.1 to 2 percent by weight, based on the amount of solvent employed. Working up is effected by customary methods. In general, a procedure is followed in which the reaction mixture is concentrated by distilling off the diluent under reduced pressure, water and a solvent of low water-miscibility are added to the residue which remains and the organic phase is separated off, dried and concentrated.

Instead of the compounds of the formula (II), it is also possible to use mixtures of compounds of the formulae (I) and (II) in carrying out the process according to the invention.

The β-hydroxyethyl-(1,2,4-triazole) derivatives of the formula (I) which can be prepared by the process according to the invention are known (compare EP-OS (European Published Specification) No. 40,345, EP-OS (European Published Specification) No. 44,605, EP-OS (European Published Specification) No. 46,337, EP-OS (European Published Specification) No. 47,594, EP-OS (European Published Specification) No. 52,424 and DE-OS (German Published Specification) 2,654,890). They are distinguished by very good plant growth-regulating and fungicidal properties.

The process according to the invention is illustrated by the following examples.

EXAMPLE 1

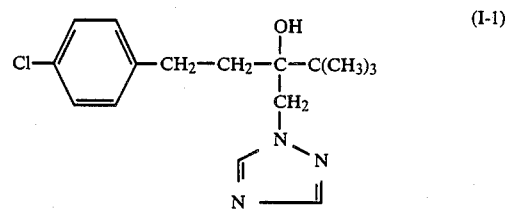

(I-1)

(a) 3 g (9.74 mmol) of 1-(4-chloro-phenyl)-4,4-dimethyl-3-(1,3,4-triazol-1-yl-methyl)-pentan-3-ol were suspended in 2 ml of N-methylpyrrolidone, and 40 mg (1 mmol) of sodium hydroxide were added. The reaction mixture was heated at 120° C. for 8 hours, with stirring, and was then allowed to cool, and was worked up by a procedure in which the solvent was distilled off under reduced pressure, water and methylene chloride were added to the residue which remained and the organic phase was then separated off and, after drying, was concentrated by stripping off the solvent. After washing with a little benzine, 2.6 g of a product which, according to analysis by HPLC, consisted of 1-(4-chloro-phenyl)-4,4-dimethyl-3-(1,2,4-triazol-1-yl-methyl)-pentan-3-ol to the extent of 98%, were obtained. The yield is accordingly calculated as 84.9% of theory.

It was shown, by analysis by HPLC, that the product was not contaminated by the corresponding 1,3,4-triazole derivative.

(b) In another embodiment, the reaction described above was repeated, but a spatula-tip of azobisisobutyronitrile was added to the reaction mixture.

2.95 g of a product which consisted of 1-(4-chloro-phenyl)-4,4-dimethyl-3-(1,2,4-triazol-1-yl-methyl)pentan-3-ol to the extent of 97% were obtained in this manner. The yield is accordingly calculated as 95.4% of theory.

(c) 30.8 g (0.1 mol) of 1-(4-chloro-phenyl)-4,4-dimethyl-3-(1,3,4-triazol-1-yl-methyl)-pentan-3-ol were suspended in 125 ml of N-methyl-pyrrolidone, and 4.15 g (0.104 mol) of sodium hydroxide and 1 ml of water were added. The reaction mixture was heated at 120° C. for 4 hours, with stirring, during which a dry stream of $CO_2$-free air was slowly passed through the reaction mixture. The mixture was then worked up by a procedure in which the solvent was distilled off under reduced pressure, water and methylene chloride were added to the residue which remained, and the organic phase was then separated off and, after drying, was concentrated by stripping off the solvent. 30.1 g of a product which consisted of 1-(4-chloro-phenyl)-4,4-dimethyl-3-(1,2,4-triazol-1-yl-methyl)pentan-3-ol to the extent of 96% were obtained in this manner. The yield is accordingly calculated as 93.8% of theory.

It was shown, by analysis by HPLC, that the product is not contaminated by the corresponding 1,3,4-triazole derivative.

The products listed in Table 2 which follows were also obtained by the method described under (b) in Example 1.

TABLE 2

| Example No. | R¹ | R² | Melting point (°C.) |
|---|---|---|---|
| 2 | $(CH_3)_3C-$ | H | 83–84 |
| 3 | 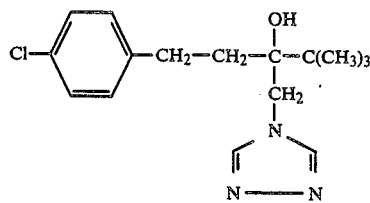 | $\begin{array}{c} CH_3 \\ | \\ -C-CH_2F \\ | \\ CH_3 \end{array}$ | 110–112 |
| 4 | 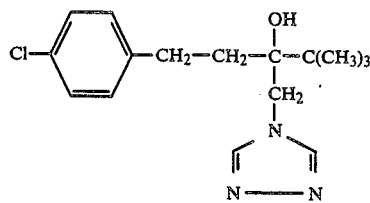 | $\begin{array}{c} -C(CH_2F)_2 \\ | \\ CH_3 \end{array}$ | 122–124 |

PREPARATION OF STARTING SUBSTANCES
EXAMPLE (II-1)

238.5 g (1 mol) of 2-(4-chloro-phenyl-ethyl)-2-tert.-butyl-oxirane, 75.9 g (1.1 mol) of 1,3,4-triazole and 4 g (0.1 mol) of sodium hydroxide lozenges were stirred under reflux in 200 ml of n-propanol for 30 hours. The reaction solution was evaporated under reduced pressure and the residue was taken up in three times the amount of ethyl acetate. The mixture was filtered at 20° C. The residue consisted chiefly of 1-(4-chloro-phenyl)-4,4-dimethyl-3-(1,3,4-triazol-1-yl-methyl)-pentan-3-ol. For further purification, the product was recrystallised from acetone. Melting point: 188° C., yield: 69 g (22.4%).

COMPARISON EXAMPLE

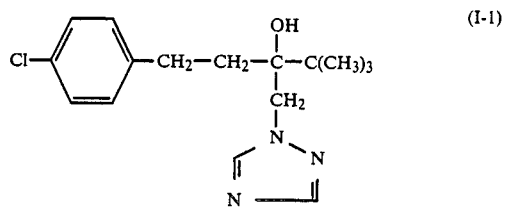

A solution of 27.1 g (0.1 mol) of a product which consisted of 2-(4-chloro-phenyl-ethyl)-2-tert.-butyl-oxirane to the extent of 88%, 8.3 g (0.12 mol) of 1,2,4-triazole and 0.6 g (0.01 mol) of potassium hydroxide in 100 ml of n-propanol was heated at 95° C. for 30 hours.

Thereafter, the reaction mixture was allowed to cool and was concentrated by stripping off the solvent under reduced pressure. The residue which remained was taken up in toluene, the suspension thereby formed was filtered and the filtrate was concentrated by stripping off the solvent under reduced pressure. The residue obtained was recrystallised from Ligroin. 30.6 g of a product which, according to analysis by HPLC, consisted of 1-(4-chloro-phenyl)-4,4-dimethyl-3-(1,2,4-triazol-1-yl-methyl)-pentan-3-ol to the extent of 67.4% were obtained in this manner. A yield of 67% of theory is accordingly calculated.

It will be understood that the specification and examples are illustrative but not limitative of the present invention and that other embodiments within the spirit and scope of the invention will suggest themselves to those skilled in the art.

What is claimed is:

1. A process for the preparation of a β-hydroxyethyl-(1,2,4-triazole) derivative of the formula

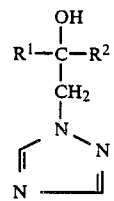

in which

R¹ is methyl, ethyl, propyl, isopropyl, n-butyl, isobutyl, sec.-butyl or tert.-butyl, or methyl, ethyl, propyl, isopropyl, n-butyl, iso butyl, sec.-butyl or tert.-butyl which is substituted by 1 to 3 fluorine and/or chlorine atoms, or represents cyclopropyl, cyclopentyl or cyclohexyl which is optionally substituted by methyl, or represents phenyl, which can be mono-, di- or tri-substituted by fluorine, chlorine, bromine, methyl, tert.-butyl, cyclohexyl, methoxy, methylthio, trifluoromethyl, trifluoromethoxy, trifluoromethylthio, phenyl which is optionally substituted by fluorine, chlorine and/or methyl, phenoxy which is optionally substituted by fluorine, chlorine and/or methyl, benzyl which is optionally substituted by fluorine, chlorine and/or methyl and/or benzyloxy which is optionally substituted by fluorine, chlorine and/or methyl, or represents phenethyl, which can be 1-, 2- or 3-substituted in the phenyl part by fluorine, chlorine, bromine, methyl, tert.-butyl, cyclohexyl, methoxy, methylthio, trifluoromethyl, trifluoromethoxy, trifluoromethylthio, phenyl which is optionally substituted by fluorine, chlorine and/or methyl, phenoxy which is optionally substituted by fluorine, chlorine and/or methyl, benzyl which is optionally substituted by fluorine, chlorine and/or methyl and/or benzyloxy which is optionally substituted by fluorine, chlorine and/or methyl, and $R^2$ is hydrogen, methyl, ethyl, propyl isopropyl, n-butyl, iso-butyl, sec.-butyl or tert.-butyl, or methyl, ethyl, propyl, isopropyl, n-butyl, iso-butyl, sec.-butyl or tert.-butyl which is substituted by 1 to 3 fluorine and/or chlorine atoms, or represents alkenyl with 2 to 6 carbon atoms, alkinyl with 2 to 6 carbon atoms, or cyclopropyl, cyclopentyl or cyclohexyl which is optionally substituted by methyl, or cyclopentenyl, cyclohexenyl, cycloheptenyl or cyclooctenyl which is optionally substituted by methyl, or represents phenyl, which can be mono-, di- or tri-substituted by fluorine, chlorine, bromine, methyl, tert.-butyl, cyclohexyl, methoxy, methylthio, trifluoromethyl, trifluoromethoxy, trifluoromethylthio, phenyl which is optionally substituted by fluorine, chlorine and/or methyl, phenoxy which is optionally substituted by fluorine, chlorine and/or methyl, benzyl which is optionally substituted by fluorine, chlorine and/or methyl and/or benzyloxy which is optionally substituted by fluorine, chlorine and/or methyl, or represents phenethyl, which can be 1-, 2- or 3-substituted in the phenyl part by fluorine, chlorine, bromine, methyl, tert.-butyl, cyclohexyl, methoxy, methylthio, trifluoromethyl, trifluoromethoxy, trifluoromethylthio, phenyl which is optionally substituted by fluorine, chlorine and/or methyl, phenoxy which is optionally substituted by fluorine, chlorine and/or methyl, benzyl which is optionally substituted by fluorine, chlorine and/or methyl and/or benzyloxy which is optionally substituted by fluorine, chlorine and/or methyl which process comprises stirring a mixture consisting essentially of a β-hydroxyethyl-(1,2,4-triazole) and a β-hydroxyethyl-(1,3,4-triazole) of the respective formulas

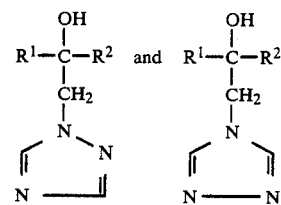

in the presence of a base and an aprotic dipolar diluent.

2. A process as claimed in claim 1, wherein the reaction is effected in the presence of water as an auxiliary solvent.

3. A process as claimed in claim 1, wherein the reaction is effected in the presence of a co-catalyst selected from the group consisting of azobisisobutyronitrile, benzoyl peroxide, air and oxygen.

4. A process as claimed in claim 1, wherein the reaction is effected at a temperature of from 50° C. to 200° C.

5. A process as claimed in claim 1, wherein the temperature is of from 70° to 150° C.

6. A process as claimed in claim 1, wherein the base is a compound selected from an alkali metal carbonate, an alkali metal hydroxide, an alkaline earth metal hydroxide, an alkaline earth metal oxide, an alkali metal alcoholate, a lower tertiary alkylamine, a cycloalkylamine and an aralkylamine.

7. A process as claimed in claim 1, wherein the aprotic, dipolar dilient is a component selected from N,N-dimethylformamide, N,N-dimethylacetamide, dimethyl sulphone, dimethylsulphoxide, hexamethylphosphoric acid triamide, phospholine oxide, sulpholane, tetramethylurea, N-methyl-pyrrolidone, N-methylhexahydropyridone, 1,3-dimethyl-hexahydro-pyrimidone and N-methyl-ξ-caprolactam.

8. A process as claimed in claim 1, wherein the mixture consists essentially of 1-(4-chlorophenyl)-4,4-dimethyl-3-(1,3,4-triazol-1-yl-methyl)-pentan-3-ol and 1-(4-chlorophenyl)-4,4-dimethyl-3-(1,2,4-triazol-1-yl-methyl)-pentan-3-ol.

9. A process as claimed in claim 1, wherein the mixture consists essentially of 1-(4-chlorophenyl)-4-methyl-4-fluoromethyl-3-(1,3,4-triazol-1-yl-methyl)-pentan-3-ol and 1-(4-chlorophenyl)-4-methyl-4-fluoromethyl-3-(1,2,4-triazol-1-yl-methyl)-pentan-3-ol.

* * * * *